United States Patent [19]

Pascale et al.

[11] Patent Number: 5,302,299
[45] Date of Patent: Apr. 12, 1994

[54] BIOLOGICAL SEMI-FLUID PROCESSING ASSEMBLY

[75] Inventors: Frank R. Pascale, Glen Cove; Thomas J. Bormann, Melville; Vlado I. Matkovich, Glen Cove, all of N.Y.

[73] Assignee: Pall Corporation, Glen Cove, N.Y.

[21] Appl. No.: 854,588

[22] Filed: Mar. 20, 1992

Related U.S. Application Data

[63] Continuation-in-part of Ser. No. 820,608, Jan. 21, 1992, which is a continuation-in-part of Ser. No. 528,160, May 24, 1990, Pat. No. 5,126,054.

[51] Int. Cl.$^5$ .................................................. B01D 37/00
[52] U.S. Cl. ........................................ 210/767; 210/436; 210/472
[58] Field of Search .................. 436/18; 210/436, 472, 210/651, 652, 772, 767; 530/395; 435/34

[56] References Cited

U.S. PATENT DOCUMENTS

| | | | |
|---|---|---|---|
| 2,781,064 | 2/1957 | Dawkins | 141/54 |
| 2,834,730 | 5/1958 | Painter, Jr. et al. | 210/446 |
| 3,149,758 | 9/1964 | Bush et al. | 222/189 |
| 3,364,658 | 1/1968 | Walker | 55/171 |
| 3,394,533 | 7/1968 | Li et al. | 55/337 |
| 3,448,041 | 6/1969 | Swank | 210/23 |
| 3,523,408 | 8/1970 | Rosenberg | 55/159 |
| 3,593,854 | 7/1971 | Swank | 210/436 |
| 3,631,654 | 1/1972 | Riely et al. | 55/159 |
| 3,635,798 | 1/1972 | Kirkham et al. | 435/34 X |
| 3,650,093 | 3/1972 | Rosenberg | 604/123 X |
| 3,663,374 | 5/1972 | Moyer et al. | 195/103.5 |
| 3,765,536 | 10/1973 | Rosenberg | 210/445 |
| 3,803,810 | 4/1974 | Rosenberg | 55/159 |
| 3,905,905 | 9/1975 | O'Leary et al. | 210/436 |
| 3,935,110 | 1/1976 | Schmid et al. | 210/445 |
| 3,935,111 | 1/1976 | Bently | 210/446 |
| 3,954,621 | 5/1976 | Etani et al. | 210/314 |
| 4,009,714 | 3/1977 | Hammer | 128/214 |
| 4,009,715 | 3/1977 | Forberg et al. | 128/214 |
| 4,087,363 | 5/1978 | Rosemeyer et al. | 210/315 |
| 4,092,246 | 5/1978 | Kummer | 210/65 |
| 4,111,199 | 9/1978 | Djerassi | 210/314 |
| 4,115,277 | 9/1978 | Swank | 210/436 |
| 4,116,845 | 9/1978 | Swank | 210/446 |
| 4,157,967 | 6/1979 | Meyst et al. | 210/446 |
| 4,170,056 | 10/1979 | Meyst et al. | 210/446 |
| 4,223,695 | 9/1980 | Muetterties | 210/445 |
| 4,229,306 | 10/1980 | Hein et al. | 210/446 |
| 4,246,107 | 1/1981 | Takenaka et al. | 210/767 |
| 4,283,289 | 8/1981 | Meyst et al. | 210/448 |
| 4,286,963 | 9/1981 | Ledis et al. | 436/18 X |
| 4,294,594 | 10/1981 | Sloane, Jr. et al. | 55/186 |
| 4,294,599 | 10/1981 | Grovesteen et al. | 55/158 |
| 4,330,410 | 5/1982 | Takenaka et al. | 210/767 |
| 4,334,901 | 6/1982 | Ayes et al. | 210/767 |
| 4,360,435 | 11/1982 | Bellamy et al. | 210/445 |
| 4,370,381 | 1/1983 | Horikoshi et al. | 210/508 |
| 4,376,675 | 3/1983 | Perrotta | 162/145 |
| 4,416,777 | 11/1983 | Kuroda et al. | 210/782 |
| 4,422,939 | 12/1983 | Sharp et al. | 210/445 |
| 4,436,631 | 3/1984 | Graham, Jr. et al. | 210/772 |
| 4,445,991 | 5/1984 | Arbit | 210/446 |
| 4,447,220 | 5/1984 | Eberle | 494/26 |
| 4,476,023 | 10/1984 | Horikoshi et al. | 210/508 |
| 4,477,575 | 10/1984 | Vogel et al. | 436/170 |
| 4,534,757 | 8/1985 | Geller | 210/446 |
| 4,543,084 | 9/1985 | Bailey | 494/20 |
| 4,596,657 | 6/1986 | Wisdom | 210/257.1 X |
| 4,608,173 | 8/1986 | Watanabe et al. | 210/806 |

(List continued on next page.)

FOREIGN PATENT DOCUMENTS

| | | |
|---|---|---|
| 315022 | 10/1989 | European Pat. Off. |
| 370584 | 5/1990 | European Pat. Off. |
| 397403 | 11/1990 | European Pat. Off. |
| 0455215 | 11/1991 | European Pat. Off. |
| 1221625 | 2/1971 | United Kingdom |
| 1501665 | 2/1978 | United Kingdom |
| 2056301 | 3/1981 | United Kingdom |

*Primary Examiner*—Frank Spear
*Attorney, Agent, or Firm*—Leydig, Voit & Mayer

[57] ABSTRACT

The invention involves a method and apparatus for treating and administering biological fluids, particularly hyperconcentrated biological fluids.

17 Claims, 1 Drawing Sheet

U.S. PATENT DOCUMENTS

| | | | |
|---|---|---|---|
| 4,617,124 | 10/1986 | Pall et al. | 210/638 |
| 4,618,533 | 10/1986 | Steuck | 428/315.7 |
| 4,636,312 | 1/1987 | Willis | 210/416.1 |
| 4,675,117 | 6/1987 | Neumann et al. | 210/789 |
| 4,680,025 | 7/1987 | Kruger et al. | 604/6 |
| 4,701,267 | 10/1987 | Watanabe et al. | 210/806 |
| 4,714,457 | 12/1987 | Alterbaum | 210/789 |
| 4,753,739 | 6/1988 | Noble | 210/787 |
| 4,767,541 | 8/1988 | Wisdom | 210/749 |
| 4,810,378 | 3/1989 | Carmen et al. | 210/206 |
| 4,855,063 | 8/1989 | Carmen et al. | 210/749 |
| 4,861,617 | 8/1989 | Pall et al. | 210/505 X |
| 4,880,548 | 11/1989 | Pall et al. | 210/503 X |
| 4,892,668 | 1/1990 | Harmony et al. | 210/782 |
| 4,900,308 | 2/1990 | Verkaart | 604/126 |
| 4,909,949 | 3/1990 | Harmony et al. | 210/787 |
| 4,915,847 | 4/1990 | Dillon et al. | 210/737 |
| 4,915,848 | 4/1990 | Carmen et al. | 210/749 |
| 4,919,823 | 4/1990 | Wisdom | 210/749 |
| 4,925,572 | 5/1990 | Pall | 210/767 |
| 4,936,998 | 6/1990 | Nishimura et al. | 210/749 |
| 4,943,287 | 7/1990 | Carmen | 604/408 |
| 4,948,628 | 8/1990 | Montgomery | 210/445 |
| 4,985,153 | 1/1991 | Kuroda et al. | 210/782 |
| 4,997,577 | 3/1991 | Stewart | 210/445 |
| 5,028,332 | 7/1991 | Ohnishi | 210/767 |
| 5,084,558 | 1/1992 | Rausch et al. | 530/395 X |
| 5,100,564 | 3/1992 | Pall et al. | 210/782 |

OTHER PUBLICATIONS

Pall "Ultipor® I.V. Filter/Air Eliminator . . . ", Pall Biomedical Products Corporation Brochures, Aug. 1980.

"Vox Sanguins", Journal of Blood Transfusion, vol. 23, pp. 308-320, (1972).

"Pall RC50 and RC100 Leukocyte Removal Filters Bedside", Pall Biomedical Products Corp., S-RC50/RC100 Brochure.

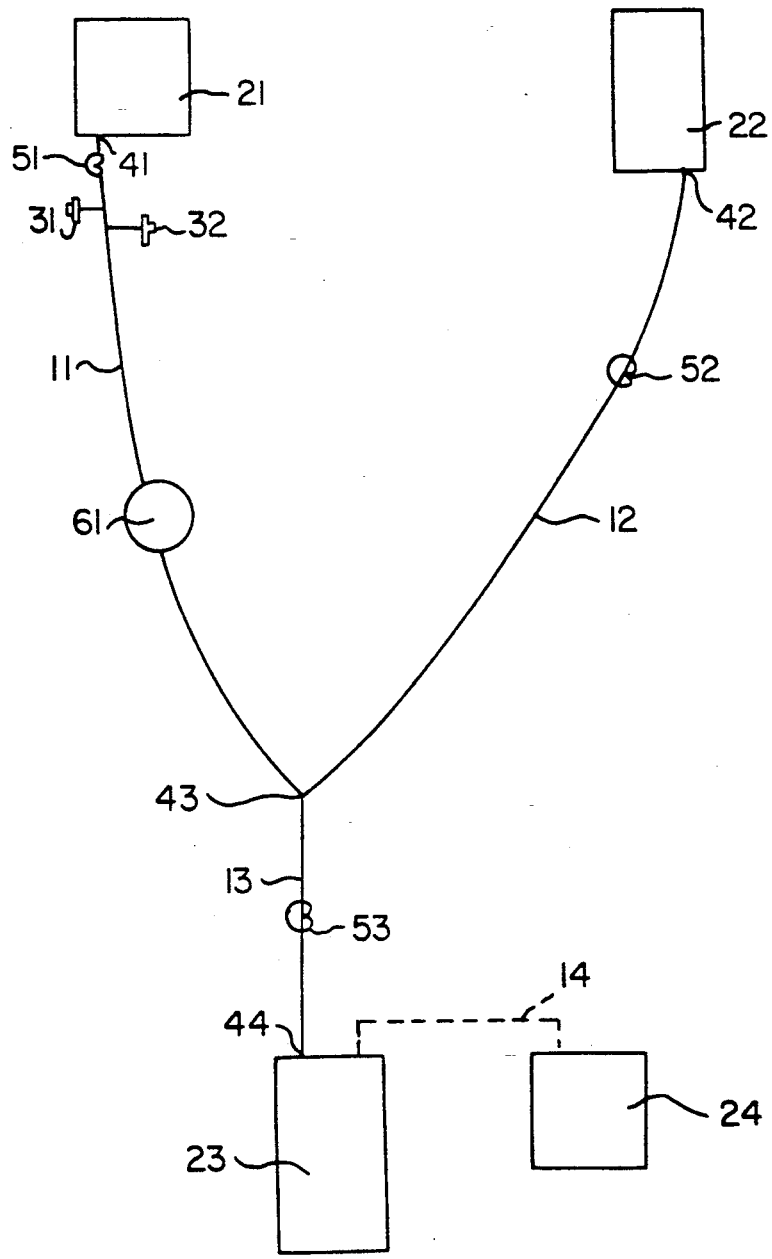

1

BIOLOGICAL SEMI-FLUID PROCESSING ASSEMBLY

This application is a continuation-in-part of U.S. Ser. No. 07/820,608, filed Jan. 21, 1992, which is a continuation-in-part of U.S. Ser. No. 07/528,160, filed May 24, 1990, now U.S. Pat. No. 5,126,054.

TECHNICAL FIELD

The invention involves a method and apparatus for treating and administering biological fluids.

BACKGROUND OF THE INVENTION

Congenital hemolytic anemias include a heterogenous group of intrinsic red cell abnormalities that are sometimes classified as disorders of hemoglobin (hemoglobinopathies and thalassemia syndromes), red cell enzyme-deficiency disorders, and abnormalities of the red cell membrane and cytoskeleton. In patients affected with any of these conditions, red cell transfusions may be indicated to compensate for the decreased oxygen-carrying capacity associated with the underlying anemia. Furthermore, red cell transfusions may also be indicated for pathophysiological consequences unique to each of these disorders. It may therefore be desirable to transfuse patients with a red cell preparation.

Red blood cells are the type of transfusion normally associated with blood transfusion. Its primary purpose concerns oxygen transfer—hemoglobin in the red cells transfers oxygen in the lungs to tissues in other parts of the body.

A typical unit of whole blood includes about 450 ml of whole blood and about 65 ml of anti-coagulant. Thus a unit of whole blood typically includes a hematocrit of about 36% to about 44%. Hematocrit typically refers to the proportion of erythrocytes in blood. A method of measuring the hematocrit may be by dividing the volume of packed erythrocytes by the volume of the specimen, and multiplying by 100.

Whole blood may be separated into its components for use in transfusions. For example, red blood cells may be prepared as a component by removing approximately 200–250 ml of plasma. This red cell component is typically referred to as packed red cells (PRC), the hematocrit of which is typically in the range from about 52% to about 60% when additives are used, and about 70% to 80% when no additives are used. Under typical storage protocols, the hematocrit of stored PRC must be maintained from about 60% to about 70% in order to retain or assure viability of the red cells. Saline washed red cells are typically prepared using automated equipment for removal of plasma, with the usual final hematocrit in the range from about 70% to 80%.

It has now been shown that it may be desirable to transfuse a red cell product having a high hemoglobin content (i.e., high hematocrit, typically above about 80%) to increase the amount of oxygen-carrying capacity in the patient. Because high hematocrit packed red cells are typically not administered, the focus in the development of leucocyte depletion devices has been on normal hematocrit red cell containing solutions, i.e, solutions containing about 36% to about 70% red cells or fewer. However, as the desirability of administering high hematocrit red cell concentrates has increased, the need for a method and apparatus for depleting leukocytes from these solutions has become apparent.

SUMMARY OF THE INVENTION

The present invention provides a method and apparatus for depleting leukocytes from a biological fluid enriched for a desired result, wherein the viscosity of the fluid reduces the effectiveness of conventional porous media, e.g., leucocyte depletion assemblies. The methods and devices according to the present invention have the added advantage of relatively low costs in time, effort, personnel, and equipment required to treat and administer the biological fluid.

BRIEF DESCRIPTION OF THE DRAWINGS

FIG. 1 is an embodiment of a biological semi-fluid treatment and administration system according to the invention.

SPECIFIC DESCRIPTION OF THE INVENTION

The present invention includes a method for treating and/or administering a biological semi-fluid comprising diluting a biological semi-fluid with a physiologically acceptable diluent; and removing leukocytes from the diluted biological semi-fluid. The leucocyte depleted, diluted biological semi-fluid may then be collected and administered directly, or the collected semi-fluid may be subjected to additional processing. The method may also include using the physiologically acceptable fluid to prime the filter assembly. The physiologically acceptable fluid may also be used to remove gas from the administration assembly, by expelling gas ahead of the column of physiologically acceptable fluid through the vent.

The present invention also involves an apparatus for treating and/or administering a biological semi-fluid comprising a first conduit having an upstream end and a downstream end; and having interposed between the ends, at least one vent and at least one functional biomedical device, such as a leucocyte removal filter assembly; said upstream end being adapted for communication with a source of biological semi-fluid, preferably a red cell containing biological semi-fluid, and at least one second conduit having an upstream end adapted for communication with a source of physiologically acceptable fluid, such as a saline solution, and a downstream end adapted for communication with the source of biological semi-fluid.

The present invention also includes a biological semi-fluid administration system comprising a first container, which is a source of biological semi-fluid, preferably a red cell containing biological semi-fluid, and more preferably, a red cell containing fluid having a high hematocrit; a second container, which is a source of a physiologically acceptable fluid; a third container, which is a receiving container, preferably of suitable size to hold both the biological semi-fluid and the physiologically acceptable fluid; said first and second containers in fluid communication with the third container; and interposed between the first container and the third container, at least one vent and at least one functional biomedical device, such as a leucocyte depletion filter assembly.

As used herein, biological semi-fluid refers to any biological fluid which has been concentrated or densified to such a degree that passing the viscous fluid or semi-fluid through a porous medium, such as a leucocyte depletion filter assembly, is deleterious, difficult or unduly time consuming. Typically, the viscosity of these semi-fluids decreases the flow rate of the semi-fluid through the system so that the processing time is too long. Furthermore, red cell containing semi-fluids exhibit greater hemolysis, due in part to the decreased flow rate and/or increased residence time in the filter assembly.

For example, the systems and devices of the present invention are particularly useful with red cell containing fluids having a high hematocrit, e.g., greater than about 70%, and in some therapeutic protocols, as high as about 80% to about 90% or greater. Included within the scope of the present invention are the use of specially prepared biological fluids wherein a specific ingredient or ingredients of the special preparation are concentrated to such a degree that the viscosity of the fluid reduces the effectiveness of passing the fluid through a porous medium or decreases flow rate through the porous medium to such an extent that passing the semi-fluid through the porous medium is unduly time consuming or harmful to the semi-fluid. For example, for some patients, it is more desirable to transfuse young red cells than to transfuse older red cells or compositions which include a blend of old and young red cells. Practitioners in the art therefore may incorporate in their transfusion regimen steps to increase the recovery of young red cells so that the transfused unit contains a higher proportion of young red cells than is normally used. These semi-fluids having hyperconcentrated red cells may have a hematocrit about 80%.

As used herein, physiologically acceptable fluid refers to any fluid or additive suitable for combination with the biological semi-fluid and suitable as a diluent. Exemplary physiologically acceptable fluids include but are not limited to preservative solutions, saline solution, an isotonic (about 0.9%) saline solution, or about a 5% albumin solution or suspension. It is intended that the present invention is not to be limited by the type of physiologically acceptable fluid used.

An exemplary method and apparatus according to the invention will now be described in reference to FIG. 1.

FIG. 1 shows first container or collection bag 21, suitable for holding a source of biological semi-fluid, preferably a biological semi-fluid having an increased hematocrit, in fluid communication with second container 22, suitable for holding a physiologically acceptable fluid, preferably a fluid suitable for diluting the biological semi-fluid, more preferably a saline solution. Receiving bag or third container 23 is preferably of suitable size to contain both the biological semi-fluid and the physiologically acceptable fluid. In a preferred embodiment first container 21, second container 22, and third container 23 are in fluid communication with each other through conduits 11, 12, and 13, all joined together at junction 43. Interposed between first container 21 and third container 23 may be a leucocyte depletion filter assembly 61, suitable for removing leukocytes from the biological semi-fluid, and at least one gas outlet. In a preferred embodiment, illustrated in FIG. 1, the system includes at least one gas outlet 31 and at least one gas inlet 32. As noted in more detail below, leucocyte depletion filter assembly 61 and vents 31 and 32 are preferably interposed in conduit 11; however these elements can be positioned in or on one of the containers, preferably first container 21. The illustrated embodiment also shows clamps 51, 52, and 53 for controlling the flow of fluid through the system, but other means for controlling the flow may be used.

The apparatus may also include container or satellite bag 24, preferably in fluid communication with container 23 through conduit 14.

An exemplary method according to the invention will now be described, using PRC as the biological semi-fluid and saline as the physiologically acceptable fluid.

With clamps 51 and 53 closed and clamp 52 open, a pressure differential is established so that saline in second container 22 flows through conduit 12 and into conduit 11 in the direction of first container 21. A simple and effective method of achieving the pressure differential is by lowering the height of first container 21 to about one meter below second container 22, although other methods of achieving the desired flow are included within the scope of the present invention.

The column of saline pushes gas in conduits 12 and 11, and in filter assembly 61 in the direction of first container 21. This gas may be expelled from the system through gas outlet 31. Once the saline solution contacts gas outlet 31, outlet 31 is inactivated or closed. Clamp 51 is then opened, and saline flows into first container 21, preferably to mix with the PRC in the container. Once a suitable amount of saline solution is added to first container 21, clamp 52 may be closed, container 21 can be positioned so that PRC diluted with saline can flow in the direction of third container 23, and clamp 53 is opened. Diluted PRC passes through leucocyte depletion filter assembly 61, where leukocytes are removed from the PRC, and the leucocyte depleted, diluted PRC may be collected in third container 23.

A method according to the invention may also include separating, typically by centrifugation, the leucocyte depleted, diluted biological semi-fluid into a supernatant layer, typically a diluent-rich solution, and a sediment layer, typically a red cell rich solution or suspension. This embodiment of the method may also include expressing the supernatant layer from the third container 23 through conduit 14 into satellite bag 24, leaving the sediment layer suitable for administration into a patient.

As shown in the Figure, the second conduit is preferably attached to the first conduit downstream of the filter assembly. However, it may be desirable to connect the second conduit to the system in other locations, e.g., upstream of the filter assembly or into the first container. These and other places of attachment are included within the scope of the present invention. It is intended that the present invention is not to be limited by the position of attachment, nor by the number of conduits being attached.

The leucocyte depletion filter assembly may include any housing containing a porous medium, preferably suitable for removing leukocytes from a biological fluid. Exemplary leucocyte depletion filter assemblies include, but are not limited to, the devices and porous media disclosed in U.S. Pat. No. 4,880,548; U.S. Pat. No. 4,925,572; U.S. Pat. No. 4,923,620; and U.S. Pat. No. 5,100,564.

The gas outlet may be any of a variety of means and devices which are capable of separating gas such as air, oxygen and the like, that may be present in a biological semi-fluid processing and administration system. The gas inlet may be any of a variety of means and devices which are capable of allowing gas, such as air, oxygen, and the like, into a biological semi-fluid processing and administration system. As used herein, gas refers to any gaseous fluid, such as air, sterilized air, oxygen, carbon dioxide, and the like; it is intended that the invention is not to be limited thereby.

Additionally, the gas inlet and gas outlet are chosen so that the sterility of the system may not be compromised, if such a condition is desirable or necessary. The gas inlet and the gas outlet are particularly suited for use in closed systems, or within about 24 hours of a system being opened. A suitable gas inlet and gas outlet may include a liquophobic porous medium with a sufficiently small pore size to preclude the ingress of bacteria into the system. Because the liquophobic porous medium is not wettable by the blood and blood product being processed in the system, gas in the system that contacts the liquophobic medium will pass through it and the blood or blood products will not be absorbed by the liquophobic porous medium. Typically, the pore size of the liquophobic porous medium will be less than 0.2 microns to provide a satisfactory bacterial barrier.

In accordance with the invention, the processing and administration system may be provided with a gas inlet to permit the introduction of air or gas into the system and/or with a gas outlet to permit gases in the various elements of the system to be separated from the system. It is intended that at least one gas inlet and/or at least one gas outlet may be used in a biological semi-fluid processing and administration system, or the respective gas inlet or gas outlet may be used alone.

To that end, a gas inlet or gas outlet may be included in any of the various elements of the assembly. By way of illustration, at least one gas inlet or at least one gas outlet may be included in at least one of the conduits used to connect the different containers, in a wall of the containers, or in a port on or in one of these containers. The gas inlet or gas outlet may also be included on or in a combination of the elements mentioned above. Also, a filter assembly may include one or more gas inlets or gas outlets. Generally, however, it is preferred to include a gas inlet or gas outlet in the first conduit or in the filter assembly. It is more preferred to include at least one gas inlet and/or at least one gas outlet in the first conduit, as close to the first end 41 as practicable. Included within the scope of the invention is the use of more than one gas inlet or gas outlet in any one conduit, in any one blood product receiving container, or in a filter assembly.

It will be apparent to one skilled in the art that the placement of a gas inlet or a gas outlet may be optimized to achieve a desired result. For example, it may be desirable to locate the gas inlet upstream of a functional medical device and in or as close to the first container 21 as is practical in order to maximize the recovery of blood product. Similarly, it may be desirable to locate the gas outlet upstream of a functional medical device and in or as close to the first container 21 as is practical in order to maximize the volume of gas that is removed from the system. Such placement of the gas inlet or gas outlet is particularly desirable where there is only one gas inlet or gas outlet in the system.

The gas inlet and the gas outlet may be any porous medium designed to allow gas to pass therethrough. For the sake of convenience and clarity, the porous medium in the gas inlet or gas outlet shall be referred to hereinafter as a membrane.

The gas inlet of the present invention preferably includes a microporous membrane in a housing. The gas inlet may comprise a microporous membrane having both liquophobic and liquophilic layers, as described below, or may comprise other structures which allow gas to enter the system, but do not allow contaminants to enter. In a preferred embodiment, the microporous membrane is preferably liquophobic, that is, it is non-wettable. The membrane may also be liquophilic, but means should be included to keep the liquophilic membrane dry until ready for use. For example, while the biological semi-fluid is being processed through the system, a clamp or other closure mechanism (such as a cap or sufficient pressure differential) may be used to avoid wetting the liquophilic membrane. As used herein, liquophilic refers to a porous medium which is wetted by the liquid being processed. The liquophilic membrane is capable of passing gas therethrough so long as it remains unsaturated by the liquid being processed.

The term liquophobic as used herein is effectively the obverse of the term liquophilic; that is, a porous liquophobic material has a critical wetting surface tension lower than the surface tension of the applied liquid and is not readily or spontaneously wetted by the applied liquid. Liquophobic materials may be characterized, then, by a high contact angle between a drop of liquid placed on the surface, and the surface. Such high contact angle indicates poor wetting.

In accordance with the invention, gas may be removed from the biological semi-fluid processing assembly or from in contact wit a biological semi-fluid by passing the air or gas through a gas outlet. The gas outlet may comprise a liquophobic membrane as described above, or may comprise other structures which allow gas to pass, but do not allow contaminants to enter. In a preferred embodiment, the gas outlet includes a multi-layer microporous membrane in a housing. The first layer of the microporous membrane is preferably liquid-wettable, i.e., liquophilic, as noted above. The liquophilic membrane is capable of passing gas therethrough so long as it remains unsaturated by the liquid being processed. The second microporous membrane layer is preferably not wettable by the liquid being processed by the delivery system, that is, the second layer is liquophobic.

The liquophilic layer of a multi-layer porous medium is preferably positioned in the housing to the inward side of the gas outlet so that the liquophilic layer is in direct communication with a conduit in which the gas outlet is to be carried. In this way the liquophilic layer is the first layer to be contacted either by gas that is to be passed from the liquid transfer or delivery system or by the liquid being transferred or delivered by the system.

The liquophobic layer is also capable of passing gas therethrough. The liquophobic layer may be superimposed on the liquophilic layer, preferably positioned on the outward side of the gas outlet. The liquophobic layer is thus not contacted by either gas or liquid in the delivery system until the gas or liquid has passed through the liquophilic layer. Because of the liquid-wettable character of liquophilic layer and the non-wettable character of liquophobic layer, gas that contacts the gas outlet passes through the gas outlet so long as the liquophilic layer remains unwetted by liquid. Once the liquophilic layer becomes wetted with liquid, gas is no longer able to pass through the liquophilic layer so the gas outlet becomes sealed or inactivated. Accordingly, after the liquophilic layer is wetted by the liquid being processed, gas from outside the delivery system is foreclosed from entering the system through the gas outlet. The combined liquophobic and liquophilic membrane is particularly advantageous when the gas outlet is used in a closed sterile system; once any gases present in the system are vented, unwanted gases cannot reenter the closed system through the gas outlet.

It will be appreciated that the liquophilic and liquophobic layers may be two separate layers, or they may be bonded together. In addition, the invention contemplates the use of a plurality of separate membrane elements combined together to form the liquophilic microporous membrane and the use of a plurality of separate membrane elements combined together to form the liquophobic microporous membrane. By the term plurality is meant two or more. The plurality of separate membrane layers may be individually prepared and bonded together by various means known to those skilled in the art. For example, the separate membrane layers may be bonded together by drying two or more layers maintained in close contact. By way of example, the separate membrane layers may be prepared by passing the material used to form the membrane over a hot drum, against which the membrane is firmly held by a tensioned felt web or other process sheet. In addition, it is likewise possible to combine a suitable supporting substrate with the membrane layer, if desired, and the supporting substrate may serve as a permanent support.

In accordance with the invention the liquophobic microporous membrane must have sufficient liquophobicity with respect to the liquid to be processed such that it will be wetted by the liquid sufficiently to prevent the passage of gas after it is wetted. It is preferred that both the liquophilic and liquophobic microporous membranes have, when combined for use in the gas outlet, an overall pore size such that the membranes form a bacterial barrier. When the pore size of the microporous membranes is so chosen, the intrusion of bacteria into the system through the gas outlet is prevented. It will be readily appreciated that a gas outlet so configured is particularly well adapted for a closed system and/or for sterile liquid processing systems. Preferably, particularly in medical applications, the system is gamma—sterilizable. Such gas outlet can even be used without a cap, if desired, although it is within the purview of the invention to cap the gas outlet if desired.

The microporous membrane may be made from a variety of materials. The gas inlet and the gas outlet are porous media designed to allow gas to pass therethrough. A variety of materials may be used to form the porous media provided the requisite properties of the particular porous medium are achieved. These include the necessary strength to handle the differential pressures encountered in use and the ability to provide the desired filtration capability while providing the desired permeability without the application of excessive pressure. In a sterile system, the porous medium should also preferably have a pore rating of 0.2 micrometer or less to preclude bacteria passage. The porous medium may be, for example, a porous fibrous medium, such as a depth filter, or a porous membrane or sheet. Multilayered porous media may be used, for example, a multilayered porous membrane with one layer being liquophobic and the other liquophilic.

Preferred starting materials are synthetic polymers including polyamides, polyesters, polyolefins, particularly polypropylene and polymethylpentene, perfluorinated polyolefins, such as polytetrafluoroethylene, polysulfones, polyvinylidene difluoride, polyacrylonitrile and the like, and compatible mixtures of polymers. The most preferred polymer is polyvinylidene difluoride. Within the class of polyamides, the preferred polymers include polyhexamethylene adipamide, poly-ε-caprolactam, polymethylene sebacamide, poly-7-aminoheptanoamide, polytetramethylene adipamide (nylon 46), or polyhexamethylene azeleamide, with polyhexamethylene adipamide (nylon 66) being most preferred. Particularly preferred are skinless, substantially alcohol-insoluble, hydrophilic polyamide membranes, such as those described in U.S. Pat. No. 4,340,479.

Other starting materials may also be used to form the porous media of this invention including cellulosic derivatives, such as cellulose acetate, cellulose propionate, cellulose acetate-propionate, cellulose acetate-butyrate, and cellulose butyrate. Non-resinous materials, such as glass fibers, may also be used.

It will be appreciated that if the material chosen is normally liquophobic, and it is desired to use this material for the liquophilic microporous membrane, then the normally liquophobic material will have to be treated so as to make it liquophilic. The nature of the material used to make the membranes, the compatibility of the materials chosen for the membranes with one another and with the liquid to be processed all are factors to be considered in selecting a particular material for a membrane for a given end application. However, quite apart from those considerations, it is generally desirable and preferable that the same material be used for both the liquophilic microporous membrane and for the liquophobic microporous membrane so as to facilitate the bonding of the two different membranes to one another, if desired, as is preferred.

As noted above, the preferred material for both the liquophilic microporous membrane and the liquophobic microporous membrane is polyvinylidene difluoride. Since polyvinylidene difluoride is liquophobic, it must be treated in order to render it liquophilic. Various treatments of the normally liquophobic polyvinylidene difluoride to render it liquophilic are known. Exemplary treatments include gas plasma treatment, radiation treatment, and chemical treatment. However, the preferred method for making the polyvinylidene difluoride material liquophilic is to treat a liquophobic polyvinylidene difluoride microporous membrane by subjecting it to gamma radiation in the presence of a liquophilic agent, such as, for example, hydroxyethylmethacrylate (HEMA). Preferably liquophilic and liquophobic polyvinylidene microporous membranes are secured to each other by placing them in intimate contact and drying them on a drum dryer.

The rate of air flow through the microporous membrane of a gas outlet or a gas inlet can be tailored to the specific liquid transfer or delivery system of interest. The rate of air flow varies directly with the area of the membrane and the applied pressure. Generally, the area of the membrane is designed to enable the liquid transfer or delivery system to be primed in a required time under the conditions of use. For example, in medical applications it may be desirable to be able to prime an intravenous set in from about 30 to about 60 seconds. In such applications, as well as in other medical applications, the typical membrane may be in the form of a disc which has a diameter from about 1 mm to about 100 mm, preferably from about 2 mm to about 80 mm, and more preferably from about 3 mm to about 25 mm.

The pore size of the liquophilic and liquophobic microporous membranes is dependent on the liquid transfer or delivery system in which it is used, and, more particularly, whether the system is for medical or non-medical use. By way of illustration, where the gas inlet or gas outlet is to be incorporated in a system to be used for a medical application, the pore size of the liquophilic and liquophobic membranes is preferably selected so that at least one of the membranes provides a bacterial barrier to preclude entry of bacteria into the system. The pore size of the liquophilic and liquophobic microporous membranes may be the same or different. Generally the pore size of the liquophobic membrane is in the range of from about 0.02 to about 3 micrometers and the pore size of the liquophilic membrane is from about 0.04 to about 3 micrometers. Preferably the pore size of order to maintain a suitable barrier to contaminants and bacteria. It will be appreciated that the pressure required to transfer gas in or out of the processing system through the gas inlet or gas outlet of the present invention varies inversely with the pore size of the membrane. Accordingly, the choice of pore size may be determined by the application in which the gas inlet or gas outlet is used. For example, since the pressure required to pass gas through the gas outlet increases as the pore size of the membrane decreases, it may be desirable to choose a larger pore size (consistent with the other objectives of, for example, providing a bacterial barrier) where the delivery system is to be operated by hand so that the pressure required to use the system does not become too great for convenient hand use.

The housing may be constructed of rigid plastic material that is also transparent, such as polyethylene, an acrylic such as polymethyl methacrylate, polymethyl acrylate, polymethyl pentene-1, polyvinyl chloride, and vinyl chloride-vinylidene chloride copolymers. Translucent materials, such as polypropylene, polyethylene, urea-formaldehyde, and melamine-formaldehyde polymers, can also be employed. Other plastic materials that are particularly suitable are polystyrene, polyamides, polytetrafluoroethylene, polyfluorotrichloroethylene, polycarbonates, polyester, phenol-formaldehyde resins, polyvinyl butyral, cellulose acetate, cellulose acetate propionate, ethyl cellulose and polyoxymethylene resins. Polyacrylonitrile polybutadiene-styrene (ABS) is preferred. It is intended that the invention should not be limited by the type of housing being employed; other materials may be used, as well as mixtures, blends, and/or copolymers of any of the above.

A metal housing can be used. Suitable metals include stainless alloys, such as nickel, chromium, vanadium, molybdenum, and manganese alloys. The housing material should, of course, be inert to the liquids being processed.

The containers, such as source bag 21, receiving container 23 or satellite bag 24, may be constructed of any material compatible with whole blood or blood products, and are capable of withstanding a centrifugation and sterilization environment. A wide variety of these containers are already known in the art. For example, blood collection and satellite bags are typically made from plasticized polyvinyl chloride, e.g., PVC plasticized with dioctylphthalate, diethylhexylphthalate, or trioctyltrimellitate. The bags may also be formed from a polyolefin, polyurethane, polyester, or polycarbonate. It is intended that the invention is not to be limited by the construction, shape, or size of the containers.

As used herein, the tubing may be any conduit or means which provides fluid communication between the containers, and is typically made from the same flexible material as is used for the containers, preferably plasticized PVC. A seal, valve, or transfer leg closure is typically located within the tubing. A clamp or external closure device may also be used to regulate the flow of gas or biological semi-fluid through a conduit. While the length of the conduits is not critical, certain lengths may be more desirable to achieve a desired result, e.g., decreasing the amount of gas in a conduit, or facilitating handling by the technician. For example, it may be desirable to reduce the amount of gas in conduit 13. This may be accomplished by using a conduit about three lengths long (approximately 4.5 inches). It is intended that the present invention is not limited by the type of material used to construct the containers or the conduit which connects the containers.

In accordance with the invention, a clamp, closure, or the like may be positioned on or in any or all of the conduits in order to facilitate a desired function, i.e., establishing a desired flow path for biological semi-fluid or gas. For example, when processing a blood product through a system such as is illustrated in FIG. 1, during the removal of gases from conduit 11 and filter assembly 61, it may be desirable to clamp conduit 11 as close to container 21 as practical in order to maximize the amount of gas vented through gas outlet 31.

As used herein, adapted for communication refers to any means or methods for establishing fluid flow through the system. For example, two conduits may be heat sealed together, to form a sterile connection using known connection devices; or a conduit may have a connector adapted to receive or connect to a mated connector on another conduit; or the connector may be a spike, adapted to be inserted in a fluid container, such as a blood bag or the like. As used herein, connector refers to any structure used to form a joint or to join itself to another piece. These connectors establish a flow path through various elements of an assembly or system. Connector, as used herein, typically refers to penetrating connectors, such as a spike, cannula, or needle; and mating connectors, such as Luer-type, screw-type, friction-type, or connectors which are bonded together. It is intended that the present invention is not to be limited by the type of connector or connection used for establishing fluid flow through the conduit.

Pre-priming, as used herein, refers to wetting or priming the inner surfaces of an assembly prior to its actual use. For example, using the device illustrated in FIG. 1, a connector 42, such as a spike, may be inserted into container 22; the clamp 52 is opened to allow fluid to flow through the conduit 12 and filter assembly 61; then, with the passage of fluid through the assembly, gas downstream of the fluid is expelled through the gas outlet 31 until fluid reaches the outlet. With the clamp 51 in a closed position, the connector downstream of the gas outlet may be opened or readied for use without fluid in the assembly dripping through the connector.

Movement of a biological semi-fluid through the system may be effected by maintaining a pressure differential between a source bag and a destination of the biological semi-fluid (e.g., a satellite bag or a needle on the end of a conduit). Exemplary means of establishing this pressure differential may be by gravity head, applying pressure to the collection bag (e.g., by hand or with a pressure cuff), or by placing the satellite bag in a chamber which establishes a pressure differential between the satellite bag and the collection bag (e.g., a vacuum chamber).

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for treating a biological semi-fluid comprising
   diluting the biological semi-fluid with a physiologically acceptable diluent; and
   removing leukocytes from the diluted biological semi-fluid by passing the diluted biological semi-fluid through a filter assembly which removes leukocytes from the biological semi-fluid; and,
   separating a substantial portion of the diluent from the leuococyte depleted biological semi-fluid.

2. The method of claim 1 wherein treating a biological semi-fluid comprises treating a red cell containing fluid.

3. The method of claim 2 wherein treating a biological semi-fluid comprises treating packed red cells having a high hematocrit.

4. The method of claim 3 wherein treating a biological semi-fluid comprises treating a biological semi-fluid having a hematocrit above about 80%.

5. The method of claim 1 further comprising removing gas from a treatment apparatus.

6. The method of claim 5 wherein removing gas from the treatment apparatus comprises venting the gas through a gas outlet.

7. The method of claim 6 wherein removing gas from the treatment apparatus comprises venting gas displaced by diluent.

8. The method of claim 5 wherein removing gas from the treatment apparatus comprises priming the leucocyte depletion filter assembly.

9. The method of claim 8 wherein removing gas from the treatment apparatus comprises venting gas displaced by diluent.

10. The method of claim 1 further comprising recovering the leucocyte depleted diluted biological semi-fluid.

11. The method of claim 10 wherein recovering the leucocyte depleted diluted biological semi-fluid includes recovering biological semi-fluid in the filter assembly.

12. The method of claim 11 wherein recovering the leucocyte depleted diluted biological semi-fluid comprises opening a gas inlet to allow air to enter the apparatus.

13. The method of claim 1 further comprising administering the leukocyte depleted biological semi-fluid.

14. A method for treating a high hematocrit biological semi-fluid comprising
   diluting a red cell containing biological semi-fluid with a physiologically acceptable diluent;
   removing leukocytes from the diluted biological semi-fluid by passing the red cell containing biological semi-fluid through a leucocyte depletion filter assembly;
   separating a substantial portion of the diluent from the leucocyte depleted biological semi-fluid.

15. The method of claim 14 further comprising priming the leucocyte depletion filter assembly and venting gas from a treatment apparatus.

16. The method of claim 14 wherein separating a substantial portion of the diluent comprises removing sufficient diluent so that the biological semi-fluid has a hematocrit above about 80%.

17. The method of claim 14 further comprising administering the leukocyte depleted biological semi-fluid.

* * * * *

UNITED STATES PATENT AND TRADEMARK OFFICE
CERTIFICATE OF CORRECTION

PATENT NO. : 5,302,299
DATED : April 12, 1994
INVENTOR(S) : Pascale et al.

It is certified that error appears in the above-indentified patent and that said Letters Patent is hereby corrected as shown below:

On the title page,
In Item [56], please add --4,963,260  10/1990  Naoi et al. 3/89--.

In Claim 8, column 12, line 3, after "apparatus" insert --further--.

In Claim 11, column 12, line 12, after "semi-fluid" insert --retained--.

Signed and Sealed this

Sixteenth Day of August, 1994

Attest:

BRUCE LEHMAN

*Attesting Officer*     *Commissioner of Patents and Trademarks*